United States Patent
Uhl et al.

(10) Patent No.: US 7,196,787 B2
(45) Date of Patent: Mar. 27, 2007

(54) APPARATUS FOR TOTAL INTERNAL REFLECTION MICROSCOPY

(75) Inventors: Rainer Uhl, Graefeling (DE); Michael Hartl, Munich (DE)

(73) Assignee: TILL Photonics GmbH, Graefelfing (DE)

( * ) Notice: Subject to any disclaimer, the term of this patent is extended or adjusted under 35 U.S.C. 154(b) by 443 days.

(21) Appl. No.: 10/790,684

(22) Filed: Mar. 3, 2004

(65) Prior Publication Data

US 2004/0174523 A1    Sep. 9, 2004

(30) Foreign Application Priority Data

Mar. 3, 2003   (DE) ............................... 103 09 269

(51) Int. Cl.
*G02B 21/00* (2006.01)
*G01J 3/30* (2006.01)

(52) U.S. Cl. .................. 356/317; 356/318; 359/368; 359/387

(58) Field of Classification Search ................ 356/317, 356/318, 445; 359/387, 368; 250/458.1, 250/201.3
See application file for complete search history.

(56) References Cited

U.S. PATENT DOCUMENTS

| | | | | |
|---|---|---|---|---|
| 4,407,569 A | * | 10/1983 | Piller et al. ................. | 359/370 |
| 4,626,079 A | * | 12/1986 | Nakamura et al. .......... | 359/387 |
| 5,208,648 A | * | 5/1993 | Batchelder et al. ....... | 356/237.1 |
| 6,259,557 B1 | * | 7/2001 | Miyashita et al. .......... | 359/387 |
| 2002/0097489 A1 | | 7/2002 | Kawano et al. | |

* cited by examiner

*Primary Examiner*—Layla G. Lauchman
(74) *Attorney, Agent, or Firm*—David S. Safran

(57) ABSTRACT

An apparatus for total internal reflection microscopy of a sample, comprising a microscope objective lens; an excitation beam path for passing light through the objective lens to said sample; and a coupling element arranged in a back focal plane of the objective lens or in a plane which is conjugate to said back focal plane; said coupling element comprising a first area for relaying light to the objective lens for total internal reflection illumination of said sample and a second area; wherein said second area is capable of separating light emitted by said sample and passing through said excitation beam path in reverse direction from said excitation beam path; wherein said second area is spatially separate from said first area and does not overlap with said first area; and wherein a distance between said optical axis of the objective lens and that boundary of said first area which is nearer to said optical axis of the objective lens is selected such that the light beams passing from said first area into the objective lens are imaged by the objective lens at angles onto said sample for which total reflection of these light beams occurs.

17 Claims, 5 Drawing Sheets

APPARATUS FOR TOTAL INTERNAL REFLECTION MICROSCOPY

BACKGROUND OF THE INVENTION

1. Field of the Invention

The present invention relates to an apparatus for total internal reflection microscopy having an objective lens and a coupling element for illuminating the specimen through the objective lens in a fashion that allows evanescent field-illumination, epi-illumination or both.

2. Description of Related Art

The principle of total internal reflection (TIR), which prevents a light beam exceeding a given angle of incidence from leaving a medium having a higher refractive index into a medium having a lower refractive index is increasingly utilized for epi-fluorescence microscopy ("total internal reflection fluorescence (TIRF)"). Therein the fact is utilized that the electromagnetic field of the totally reflected light beam extends into the medium having the lower refractive index and is able to excite fluorescent molecules there. The penetration depth of this so-called evanescent field depends on the wavelength "$\lambda$" and the angle of reflection "$\alpha$" and usually is about several hundred nanometers. Thus it is possible to distinguish fluorophores located close to the reflecting interface from those located further away from it. An angle sufficiently large for total reflection within the substrate can either be achieved by coupling the excitation light beam laterally into the support substrate, or by utilizing special immersion objective lenses having an extraordinarily high numerical aperture. Such objectives allow to focus light onto the specimen at an angle exceeding the threshold angle of total internal reflection.

Lasers are usually used as light sources for TIR epi-fluorescence. A diffraction limited laser focus is projected into the rear focal plane of an appropriate objective lens having a sufficiently high numerical aperture. Upon passing through the objective lens the laser light is collimated, whereby the exact focus position in the back focal plane (pupil) of the objective lens determines the angle of incidence of the beam of light on the sample according to equation 1:

$$\sin\alpha = r/(n_0 f)$$

The condition for total internal reflection, on the other hand, is given by equation 2:

$$n_0 \sin\alpha = n_1$$

wherein
- r: distance of the laser focus from the optical axis;
- $n_1$: refractive index of the specimen medium;
- $n_0$: refractive index of the substrate or the immersion medium;
- f: focal distance of the objective lens For positioning the laser focus in the desired focal position within the pupil of the objective lens the laser light usually is coupled into the beam by means of a beam splitter element. However, if the laser beam does not hit the beam splitter at the right angle or if the beamsplitter is not tilted correctly, laser light may enter areas of the pupil of the objective lens, which do not result in total reflection.

The use of a laser as a preferred light source for TIR epi-fluorescence is a consequence of the low illumination depth of the TIR arrangement. Usually only a few fluorophores are excited in the narrow evanescent field, hence the resulting signals are usually very weak. If it is not possible to increase the sensitivity of the detector, the excitation energy has to be increased for achieving a good signal to noise ratio. On the other hand, when utilizing sufficiently strong lasers, even minute changes of the adjustment of the laser beam may result in a laser beam, which doesn't undergo total internal reflection. Instead it may pass through the specimen and reach the experimenter's eye where it may cause significant and harmful damage. U.S. patent application Ser. No. 2002/0097489 A1 discloses a microscope system for TIR illumination wherein exclusively white light is used, which passes through an annular aperture prior to being coupled into the illumination beam by reflection via a separate beam splitter. This beam splitter serves to combine normal epi-illumination light with TIR illumination light. A drawback of this microscope is its relatively complicated design.

It is an object of the invention to provide for an apparatus for TIR microscopy having a coupling element for TIR illumination and simultaneously for light from another light source for epi-illumination, wherein a reliable protection from faulty operation during adjustment is achieved, wherein the apparatus is also particularly suitable for the use of lasers having a high output power, and wherein the apparatus has a particularly simple design.

SUMMARY OF THE INVENTION

This object is attained by an apparatus for TIR microscopy in accordance with the invention. The invention is beneficial in that laser light beams, which have been coupled into the apparatus under conditions which do not result in TIR—and which hence may escape from the set up with virtually no attenuation—are masked out already by the coupling element. A further benefit is the simple design, wherein the coupling element is used not only for coupling the TIR excitation light into the microscope, but simultaneously also serves to couple normal epi-illumination light into the microscope and/or for decoupling light emitted by the sample from the microscope. Thereby simultaneously another essential requirement of practical TIRF systems is achieved: it is possible to realize the option to supplement information obtained by TIRF methods by classical epi-illumination methods by simultaneously illuminating the sample with normal epi-illumination light or by illuminating the sample with normal epi-illumination light shortly after illumination of the sample with light for TIRF excitation.

BRIEF DESCRIPTION OF THE DRAWINGS

FIGS. 1A and 1B show schematically a microscope objective lens 10, which is directed towards a sample 12. The sample is supported by a transparent substrate 14 (usually made of glass). An immersion medium 16 is present between the substrate 14 and the microscope objective lens 10. A coupling element 24 is located in the back focal plane of the microscope objective lens.

Figure 1:
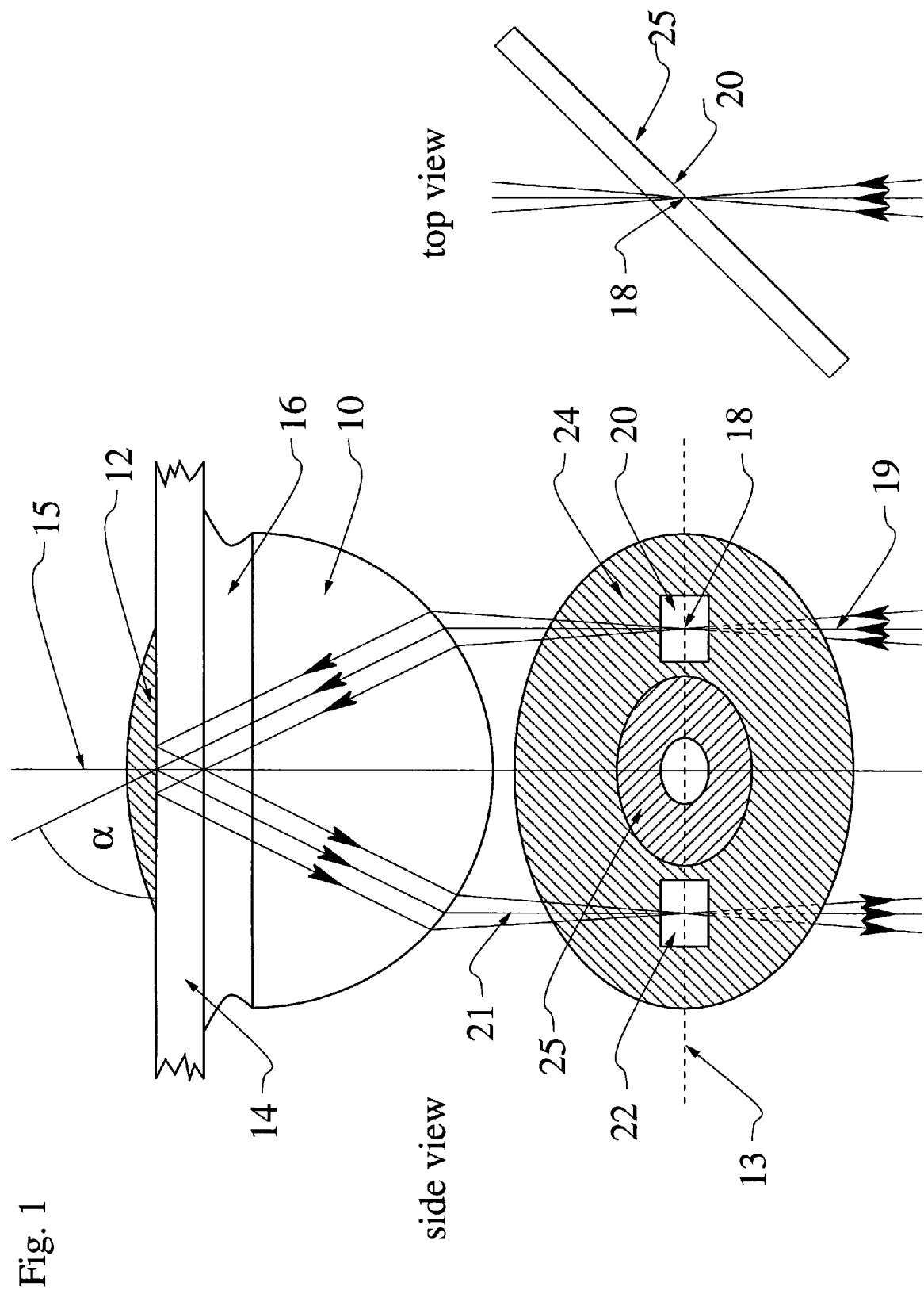
FIG. 1 is a schematic diagram of an embodiment of the invention comprising a microscope objective lens and a coupling element in the back focal plane of the microscope objective lens in side and top views.

The arrangement shown in FIGS. 1A and 1B is a system for total internal reflection (TIR) microscopy wherein TIR illumination is achieved by excitation beams 19, which are imaged onto the sample 12 by the microscope objective lens 10. The interface between the substrate 14, having a refractive index equal to that of the immersion medium 16 (usually ca. 1.5) and the sample 12 may serve as the interface where TIR occurs. Biological samples usually are embedded in water and have a refractive index of 1.33 to 1.36. The resulting threshold angle of total reflection is 62.5° to 65°.

The incident light beams 19 for the TIR illumination are brought into focus 18 at a first TIR illumination light transmitting area 20 of the coupling element 24 and are subsequently collimated by the microscope's objective lens 10 such that they point towards the substrate 14. The first area 20 is slit-shaped. The angle of incidence α between the (quasi-) parallel beams leaving the objective lens 10 and the optical axis 15 is determined by the radial distance of the focus 18 in the back focal plane of the objective lens from the optical axis 15. The larger the distance from the axis 15, the larger is the angle of incidence α1 see also equation 1.

The first area 20 of the coupling element 24 is transparent for the laser light, with the boundaries of the first area 20 being selected such that only laser light is transmitted which can reach—due to its radial distance from the optical axis 15—the substrate at angles which warrant TIR to occur. This is beneficial in that thereby it is ensured that no laser light may pass through the sample which could possibly deteriorate the signal to noise ratio of the measurement or which could endanger the operator.

The coupling element 24 is tilted relative to an axis 13 perpendicular to the optical axis 15. The axis 13 passes through the first area 20 and a further area 22, whose position is symmetrical to area 20 with respect to the optical axis 15. The coupling element 24 comprises a second area 25 in its central inner part. In case this second area 25 of the coupling element is reflective for the selected epi-illumination light, a widefield epi-illumination beam may be combined with the TIRF illumination beam. Both then, after passing the objective lens, illuminate the sample. Given that this beam occupies a circular area in the objective's back focal plane, which corresponds to angles of incidence below the critical angle, it serves for normal epi-fluorescence illumination e. In an inverted version of the above set up the laser light for TIR may be reflected by a slit-shaped reflecting area on the coupling element and the classical epi-illumination light is transmitted.

The second area 25 may be utilized in an analogous manner for reflecting light emitted by the sample 12 due to the TIR- or widefield epi-illumination from the optical axis 15. To this end the second area 25 would be reflective for the emitted light.

Totally reflected laser light 21 is refocused by the objective lens 10 and passes through area 22.

Figure 2:
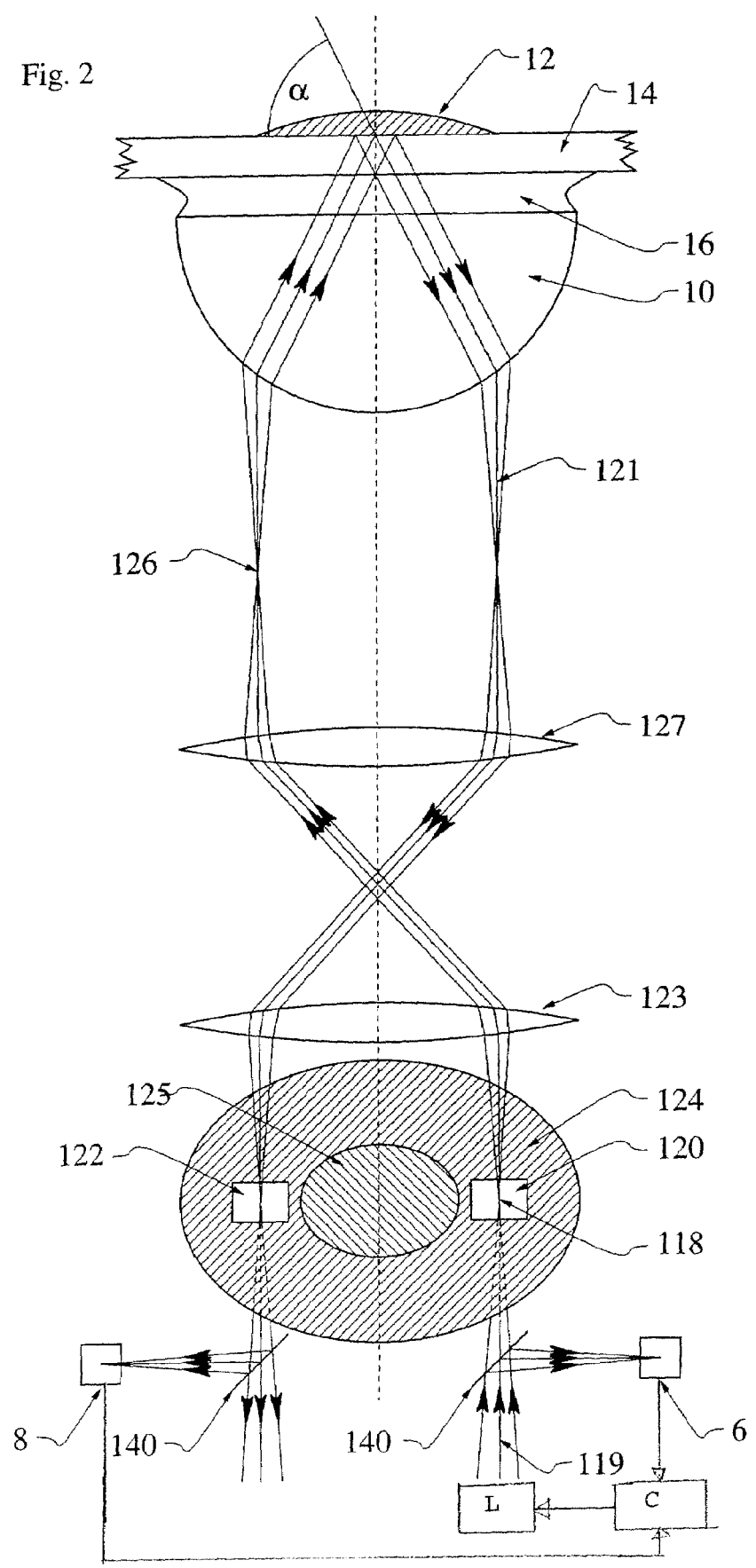
FIG. 2 schematically shows a further embodiment comprising a coupling element in a plane conjugate to the back focal plane.

According to the alternative embodiment shown in FIG. 2 a coupling element 124 is located in a conjugate plane of the back focal plane of the microscope objective lens 10. This arrangement has several advantages: it facilitates the separation of the emitted light from the excitation beam and it makes the coupling element 124 more easily accessible than it is the back focal plane of the objective.

The back focal plane of the objective and all conjugate planes thereof allow the combination of beams, which are meant to reach the sample under different angles, by the fact that the beams occupy different regions of this plane. Thus different illumination light beam paths may be combined in these planes without the use of beam splitter elements which are usually employed for this purpose. In the example shown in FIG. 2 the incident laser light 119 for TIR illumination from the light source L is focused onto a first area 120 of the coupling element 124, with the first area 120 being transparent for the TIR illumination light. The focal spot 118 achieved thereby is imaged into a focus 126 in the back focal plane of the microscope objective lens 10 by utilizing two lenses 123 and 127. The further optical beam path is identical to that shown in FIG. 1. By providing a reflective second area 125 a beam for wide field epi illumination may be combined with the focused beam used for TIR-illumination.

In FIG. 2 two detectors 6 and 8 are schematically shown. Detector 6 serves to measure a signal, which is proportional to the power of the TIR illumination light 119, and detector 8 serves to measure the power of the totally reflected light 121, which, after being reflected backwards in a symmetrical fashion, passes an area 122, corresponding to area 120 in the illumination path. Only a small fraction of both forward- and back-reflected beam is needed, it can be provided by a suitable beam splitter 140. If the ratio of these two measured power values do not match, indicating that no total internal reflection occurs or occurs only partially, a protective shut-down unit reduces the laser intensity down to levels which are safe to the operator. The shut-down unit can be incorporated into a control C that is capable of maintaining the intensity of the light for total internal reflection illumination of said sample below a pre-determined threshold intensity if a ratio between the intensity of the light for total internal reflection illumination of the sample and the intensity of the light totally reflected by the sample exceeds a predetermined threshold ratio.

By choosing an appropriate material, thickness and angle of the beam splitter 140, which uses a small fraction of the excitation beam to monitor its power, a wavelength-dependent beam-displacement in the plane of the coupling element 124 and hence of the objective's 10 back focal plane can be introduced, which compensates the wavelength-dependence of the penetration depth of the evanescent field in the sample 12. Thus a wavelength-independent penetration depth in the sample 12 can be maintained.

Figure 3:
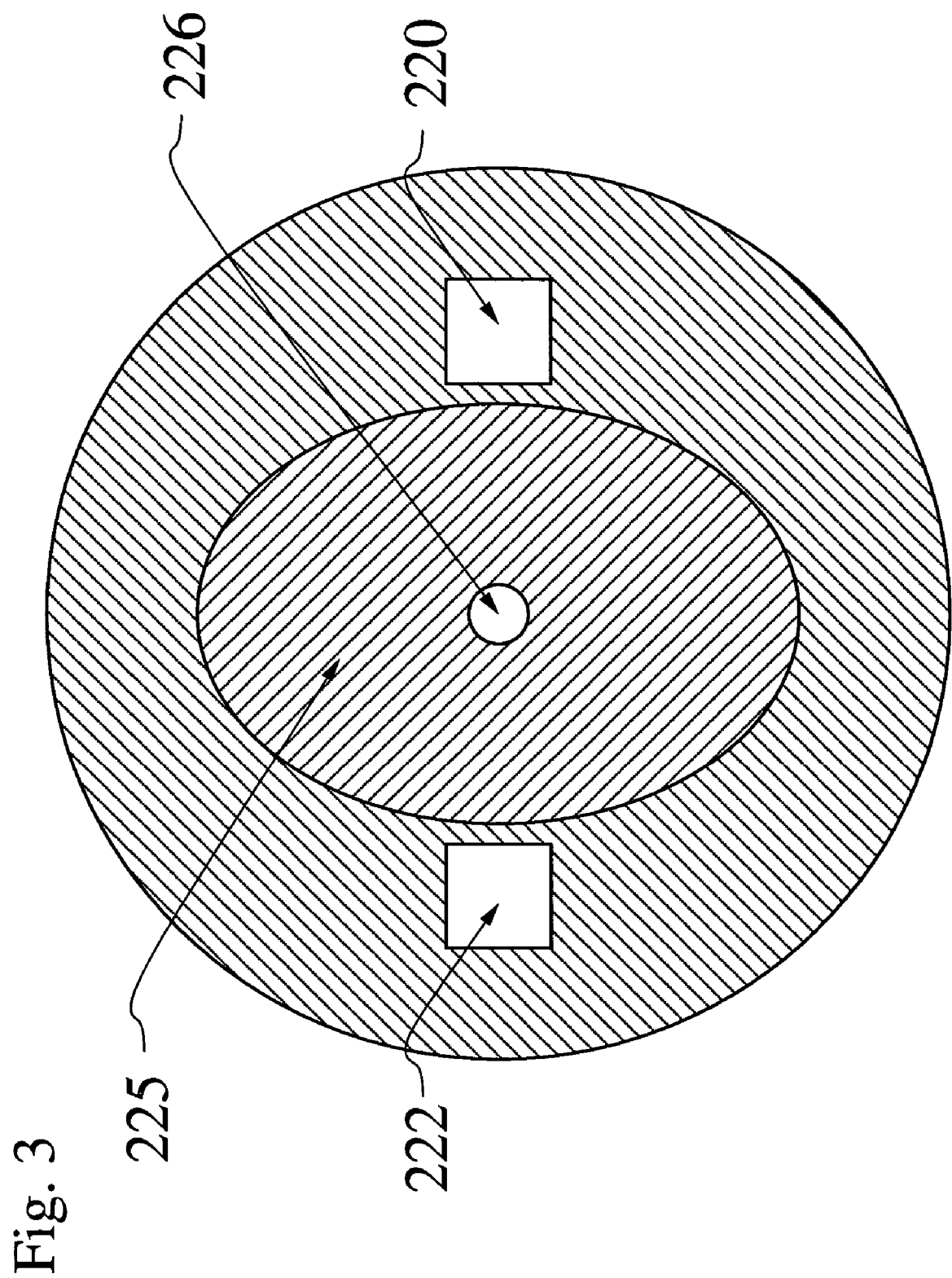
FIG. 3 is a front view of a disc-like embodiment of a coupling element for laser light.

FIG. 3 shows a front view of an embodiment of a coupling element for laser light for TIR illumination. A first area transmitting the TIR illumination light is limited to two slit-like strips 222 and 220 in the outer periphery, corresponding to regions where the numerical aperture (NA) exceeds 1.35. The laser light for illumination of the sample is focused onto slit 220. Slit 222 then serves to allow light to pass backwards after having been totally reflected at the sample. The coupling element shown in FIG. 3 is adjusted in the optical axis of the microscope in a tilted orientation relative to the optical axis in the same manner as the coupling element 124 shown in FIG. 2. A second area reflecting the epi-illumination light comprises an inner ellipse 225 whose projection yields a circular area having a diameter corresponding to the numerical aperture of the objective lens utilizable by the epi-illumination. For watery media this corresponds to the range between a numerical aperture of 0 and a numerical aperture of 1.35. For achieving easy adjustment and centering it may be beneficial to provide for a transparent opening 226 in the inner reflecting circle. Due to its small size opening 226 does not significantly affect the light yield of the normal illumination light beam.

The version of the coupling element described so far is particularly suitable for the use of laser light for TIRF excitation. However, if one wishes to make use of the flexibility of a non-coherent light source, which is not limited to only a few laser lines, an intensity problem will arise. In order to overcome this problem not only a single illumination beam, but rather a bundle of beams, all having an angle larger than the angle of total reflection has to be utilized. All "utilizable" beams have to pass an annular ring in the back focal plane of the objective lens, having an inner radius $r_g$ corresponding to the threshold angle of total reflection and having an outer radius $r_o$ corresponding to the maximum angle of the objective lens (i.e. corresponding to the numerical aperture of the objective lens).

Figure 4:
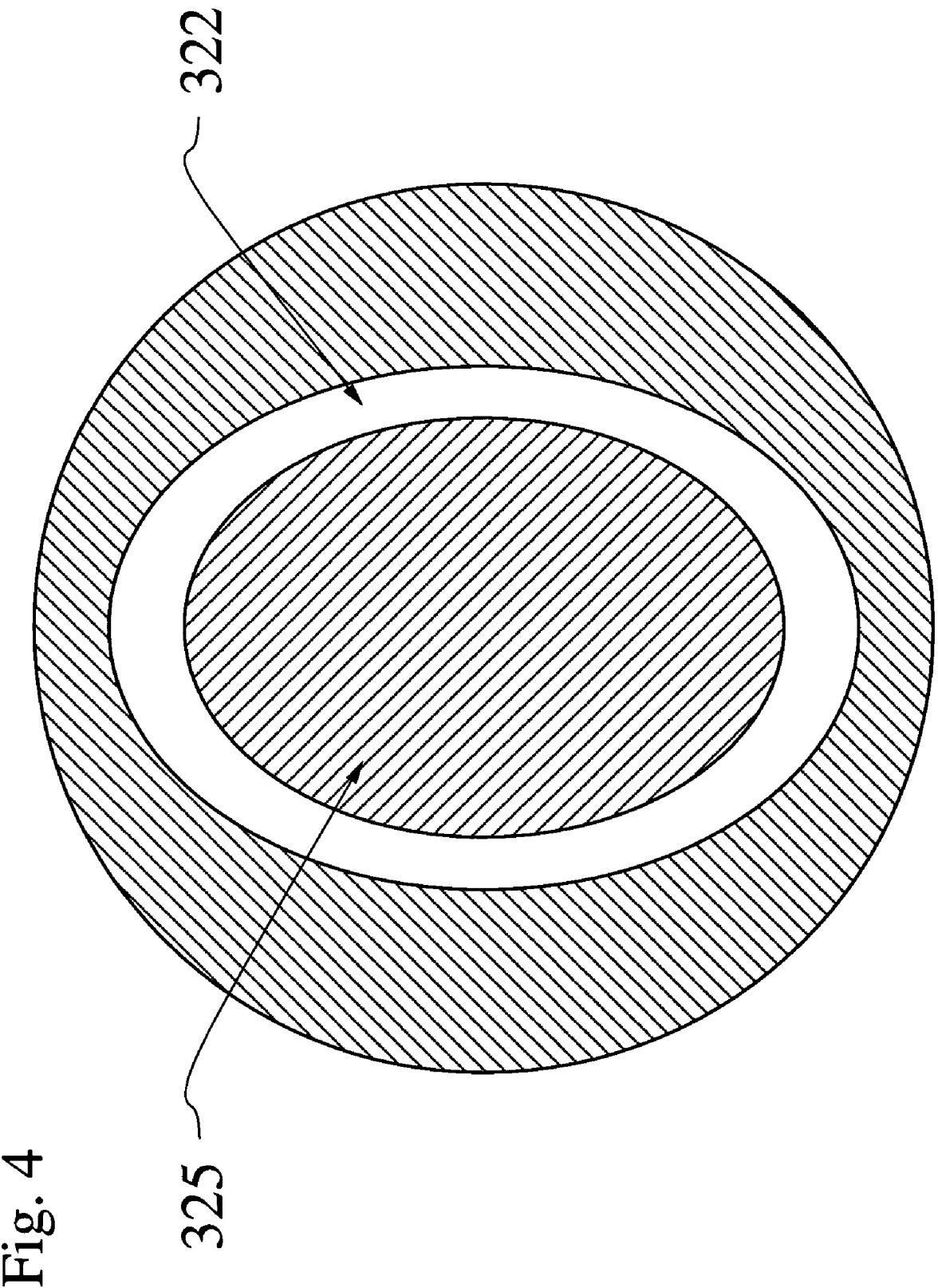
FIG. 4 is a front view of a disc-like embodiment of a coupling element for non-coherent light.

FIG. 4 shows a disc-like embodiment of a coupling element for non-coherent light. A first area, which is transparent for the light for TIR illumination, is limited to a ring 322 in the outer periphery corresponding to a numerical aperture of more than 1.35. The illumination light is focused onto ring 322. A second area, which is reflective for the light of an epi-illumination, comprises an inner oval 325 corresponding to the projection of the numerical aperture of the objective lens utilizable by the epi-illumination light.

Figure 5:
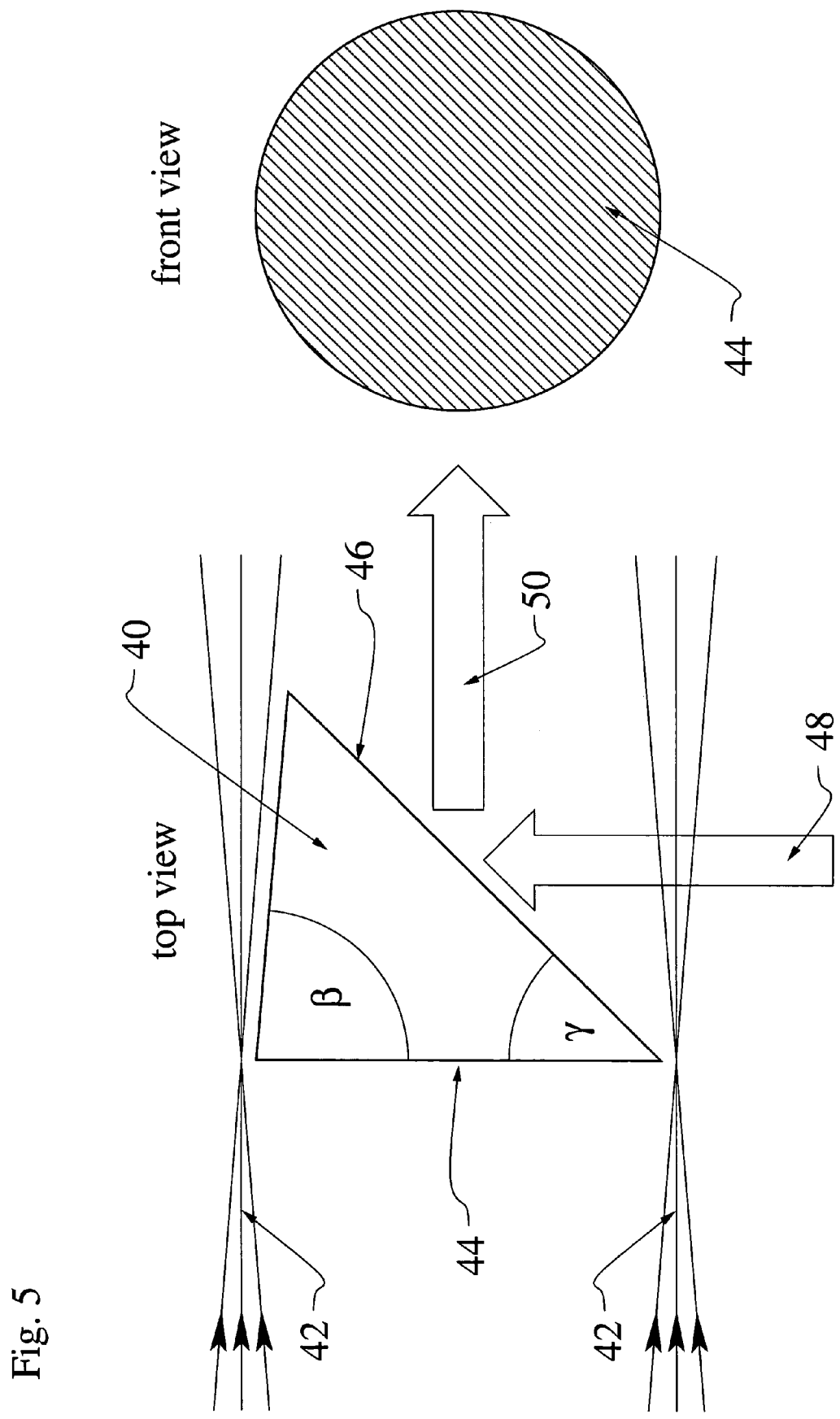
FIG. 5 is a schematic diagram of an embodiment of an embodiment of a coupling element for non-coherent light having the shape of a cut cone in top and front views.

FIGS. 5A and 5B show an alternative embodiment of a coupling element for non-coherent light, comprising a body 40 having the shape of a cone having an envelope oriented at an angle β relative to the base and having a tip, which is cut at an angle Γ relative to the base light beams 42 for TIR illumination are prevented by the circular reflecting base surface 44 from reaching the sample at angles which are smaller than the threshold angle of total reflection. The elliptically shaped sectional surface 46 likewise is reflective for coupling incident light 48 for epi-illumination into the microscope objective lens 10 along the share 50 of illumination light beams.

Although the coupling element 24, 124 preferably is tilted relative to the optical axis, this is not a mandatory feature. Rather the coupling element might be designed such that the transmission through the second area is wavelength dependent in such a manner that the light for TIR illumination is not transmitted, while the light for epi-illumination or the light emitted by the sample is transmitted.

What is claimed is:

1. An apparatus for total internal reflection microscopy of a sample, comprising
   a microscope objective lens;
   an excitation beam path for passing light through the objective lens to said sample; and
   a coupling element arranged in a back focal plane of the objective lens or in a plane which is conjugate to said back focal plane;
   said coupling element comprising a first area for relaying light to the objective lens for total internal reflection illumination of said sample and a second area; wherein said second area is capable of separating light emitted by said sample and passing through said excitation beam path in reverse direction from said excitation beam path or said second area is capable of relaying light into an illumination path for epi-illumination of said sample or said second area is capable of both separating light emitted by said sample and passing through said excitation beam path in reverse direction from said excitation beam path and relaying light an illumination path for epi-illumination of said sample; wherein said second area is spatially separate from said first area and does not overlap with said first area; and wherein a distance between an optical axis of the objective lens and that boundary of said first area which is nearer to said optical axis of the objective lens is selected such that the light beams passing from said first area into the objective lens are imaged by the objective lens at angles onto said sample for which total reflection of these light beams occurs.

2. The apparatus according to claim 1, wherein the light for total internal reflection illumination of said sample is laser light.

3. The apparatus according to claim 2, wherein said first area is transparent for said laser light.

4. The apparatus according to claim 3, wherein said second area is reflective with respect to light emitted from said sample or wherein said second area is reflective with respect to light for epi-illumination of said sample.

5. The apparatus according to claim 4, wherein said first area is an aperture in a reflecting disc.

6. The apparatus according to claim 1, wherein said coupling element is tilted relative to said back focal plane of the objective lens or relative to a plane that is conjugated relative to said back focal plane.

7. The apparatus according to claim 1, wherein said first area is formed as a first portion having a slit-like shape and extending radially relative to said optical axis of the objective lens.

8. The apparatus according to claim 7, wherein said coupling element comprises a second portion which is arranged point-symmetric with respect to said first portion relative to said optical axis of the objective lens for transmitting or reflecting laser light which has been passed onto said sample via said first portion and which has been totally reflected by said sample.

9. The apparatus according to claim 8, wherein said coupling element is tilted around an axis passing through the center of said first portion and said second portion and is tilted relative to said back focal plane of the objective lens or relative to said plane conjugated to said back focal plane.

10. The apparatus according to claim 1, wherein said coupling element has the shape of a circular or elliptical disc.

11. The apparatus according to claim 10, wherein said first area of said coupling element radially extends only over distances which correspond to a numerical aperture of more than 1.35 in a conjugated focal plane of said microscope objective lens.

12. The apparatus according to claim 1, wherein the center of said coupling element has a region for illuminating the objective lens with total internal reflection illumination laser light for adjusting said apparatus.

13. The apparatus according to claim 1, wherein light beams for total internal reflection illumination of the sample reaching said coupling element and light beams for epi-illumination of said sample reaching said coupling element are oriented at an angle of about 90°.

14. The apparatus according to claim 1, wherein a means for determining the intensity of the light for total internal reflection illumination of said sample, a means for determining the intensity of the light totally reflected by said sample and a control means are provided, wherein said control means is capable of maintaining the intensity of the light for total internal reflection illumination of said sample below a pre-determined threshold intensity if a ratio between the intensity of the light for total internal reflection illumination of said sample and the intensity of the light totally reflected at said sample exceeds a predetermined threshold ratio.

15. The apparatus according to claim 14, wherein an optical element is arranged in said excitation beam path which is capable of reflecting a portion of incident light beams for total internal reflection illumination of said sample to said means for determining the intensity of the light for total internal reflection illumination of said sample, said optical element being capable of transmitting the remainder of the incident light beams for TIR illumination of said sample to said first area of said coupling element.

16. The apparatus according to claim 14, wherein the material, the thickness and the angle of said optical element relative to said optical axis is selected such that a wavelength-dependent beam displacement in the plane of said first area of said coupling element is achieved which compensates at the sample the wavelength-dependence of the penetration depth of the evanescent field of the incident light beams for total internal reflection illumination of said sample.

17. The apparatus according to claim 1, wherein said apparatus is capable of performing fluorescence observation of said sample.

\* \* \* \* \*